(12) United States Patent
Angelides (10) Patent No.: US 8,812,244 B2
(45) Date of Patent: *Aug. 19, 2014

(54) PERSONALIZED WIRELESS-BASED INTERACTIVE DIABETES TREATMENT

(75) Inventor: Kimon Angelides, Houston, TX (US)

(73) Assignee: EOS Health, Inc., Houston, TX (US)

( * ) Notice: Subject to any disclaimer, the term of this patent is extended or adjusted under 35 U.S.C. 154(b) by 205 days.

This patent is subject to a terminal disclaimer.

(21) Appl. No.: 13/485,849

(22) Filed: May 31, 2012

(65) Prior Publication Data

US 2012/0231431 A1    Sep. 13, 2012

Related U.S. Application Data

(63) Continuation-in-part of application No. 12/693,849, filed on Jan. 26, 2010.

(60) Provisional application No. 61/147,157, filed on Jan. 26, 2009.

(51) Int. Cl.
| | |
|---|---|
| G01N 33/48 | (2006.01) |
| G06G 7/48 | (2006.01) |
| G06F 19/00 | (2011.01) |
| A61B 5/00 | (2006.01) |
| A61B 5/145 | (2006.01) |
| G10L 15/26 | (2006.01) |

(52) U.S. Cl.
CPC ........ *G06F 19/3481* (2013.01); *G06F 19/3475* (2013.01); *A61B 5/0002* (2013.01); *G06F 19/3418* (2013.01); *G06F 19/3406* (2013.01); *A61B 5/14532* (2013.01); *G06F 19/345* (2013.01); *G06F 19/3456* (2013.01); *G10L 15/26* (2013.01)
USPC ............................................. 702/19; 703/11

(58) Field of Classification Search
None
See application file for complete search history.

(56) References Cited

U.S. PATENT DOCUMENTS

| | | | |
|---|---|---|---|
| 5,673,691 A * | 10/1997 | Abrams et al. ................ | 600/300 |
| 6,980,999 B1 * | 12/2005 | Grana ........................... | 707/803 |
| 7,999,674 B2 * | 8/2011 | Kamen ....................... | 340/572.1 |
| RE43,433 E | 5/2012 | Iliff | |
| 8,392,217 B2 | 3/2013 | Iiff | |
| 2003/0208113 A1 | 11/2003 | Mault et al. | |
| 2006/0253296 A1 * | 11/2006 | Liisberg et al. .................... | 705/1 |
| 2008/0294024 A1 * | 11/2008 | Cosentino et al. ............. | 600/309 |
| 2009/0006129 A1 | 1/2009 | Thukral et al. | |
| 2010/0145173 A1 | 6/2010 | Alferness et al. | |
| 2010/0268043 A1 * | 10/2010 | Yodfat et al. .................. | 600/345 |
| 2012/0059673 A1 | 3/2012 | Cohen et al. | |
| 2012/0139720 A1 | 6/2012 | Mazar et al. | |

OTHER PUBLICATIONS

Head (Alt Med Rev, 1997, 2(4), 256-281).*

(Continued)

*Primary Examiner* — Larry D Riggs, II
(74) *Attorney, Agent, or Firm* — Eric P. Mirabel (57) ABSTRACT

This is a system for integrating a system of education, monitoring and advising on glucose testing, diet, exercise and drug administration, by a wireless link, or GPRS system, using a device which is lightweight and portable (and easily carried by the patient) and which is capable of:
glucose testing and recording the results;
providing some feedback and advice from internal programs based on the results and on patient preferences; and
transmitting the glucose testing results for external recording (e.g., on a server) and external analysis, feedback and advice from the server, and for feedback and advice from an appropriately knowledgeable and health care experienced party.

13 Claims, 3 Drawing Sheets

(56) References Cited

OTHER PUBLICATIONS

Vileikyte (Current Diabetes Reports, 2008, 8, 119-125).*
Bjelakovic et al., (Acta FAC. Med. Naiss., 2005, 22(1), 43-50).*
Silverstein et al. (School Nurse News, Mar. 9-12, 2007).*
Lim et al. Improved Glycemic Control Without Hypoglycemia in Elderly Diabetic Patients Using the Ubiquitous Healthcare Service, a New Medical Information System Diabetes Care, vol. 34, Feb. 2011 p. 308-317.

* cited by examiner

Fig. 2

PERSONALIZED WIRELESS-BASED INTERACTIVE DIABETES TREATMENT

FIELD OF THE INVENTION

The invention relates to a system for managing diabetes by transmitting queries, advice and educational materials from a server to a portable device carried by the patient using a wireless link.

BACKGROUND

Complications of diabetes are serious and include kidney failure (requiring dialysis or transplant), blindness, heart disease and limb amputation. Adequate control of diabetes leads to lower risk of complications.

Modern approaches to managing diabetes primarily rely upon dietary and lifestyle management, often combined with regular ongoing blood glucose level monitoring. Diet management allows control and awareness of the types of nutrients entering the digestive system, and hence allows indirectly, significant control over changes in blood glucose levels. Blood glucose monitoring allows verification of these, and closer control, especially important since some symptoms of diabetes are not easy for the patient to notice without actual measurement.

Every patient has different reactions to diet, exercise, and drugs administered. Patients also have different complications or potential complications associated with their disease, often including one or more of: Elevated blood pressure; compromised thyroid function; circulatory abnormalities; stroke; cardiovascular disease; infection; eye health issues including cataracts; and kidney disease. Thus, diabetes management is optimally an individualized management plan, which is continuously updated and revised as patient data relating to diet, exercise, blood glucose, and drug administration changes.

Effective diabetes management therefore requires adhering to a fairly strict diet, exercise, glucose testing and drug (including insulin) administration regimen. But non-adherence to the regimen is commonplace. Kutz S M: Adherence to diabetes regimens: empirical status and clinical applications. *Diabetes Educ* 16:50-56, 1990; Johnson S B: Methodological issues in diabetes research: measuring adherence. *Diabetes Care* 15:1658-67, 1992; McNabb W L: Adherence in diabetes: can we define it and can we measure it? *Diabetes Care* 20:215-18, 1997; Weissberg-Benchell J, Glasgow A M, Tynan W D, Wirtz P, Turek J, Ward J: Adolescent diabetes management and mismanagement. *Diabetes care* 18:77-82, 1995. Ways to educate patients and increase patient awareness about the importance of strict regimen adherence can have a significant beneficial impact on patient outcomes. Where that educational effort is coupled with close monitoring and advice on glucose testing, diet, exercise and drug administration, the patient outcomes can be improved further.

What is needed is an integrated system of education, monitoring and advising on glucose testing, diet, exercise and drug administration, all in a portable and convenient form for the patient, to maximize system utilization and thus effective disease management.

SUMMARY

The most convenient form for integrating a system of education, monitoring and advising on glucose testing, diet, exercise and drug administration, is a wireless link, or GPRS system, for a device which is lightweight and portable (and easily carried by the patient) and which is capable of:

glucose testing and recording the results;
providing some feedback and advice from internal programs based on the results; and
transmitting the glucose testing results for external recording (e.g., on a server) and external analysis, feedback and advice from the server, and for feedback and advice from an appropriately knowledgeable and health care experienced party, as necessary and appropriate.

The internal programs on the device or the wireless link should also permit patient inquiries about when to administer insulin or other drugs, when and what to eat, whether to increase or decrease exertion level. The internal programs on the device or the wireless link should also provide responses to patient inquiries, and should provide general and specific advice for the patient, including taking emergency actions. Other web-based systems which allow the patient to transmit and receive the relevant data (including results of blood glucose testing) could also be used.

Advice to a patient can take the form of specific advice or commands, e.g., "administer_mg of insulin now" or "eat now." It can also take the form of education so the patient can make an informed decision on what actions, if any, should be undertaken. In one embodiment, a portable device includes "generic" messages, stored in the device memory—allowing immediate display of some messages for the patient even if a wireless link is not available (particularly, where prompt action by the patient is needed, such as injecting insulin or eating). These generic messages preferably involve generalized education and patient direction, in response to particular circumstances, feelings, or test results the patient requests information about. For example, these messages can discuss dangers of low or high blood glucose, dangers of high ketone levels, health risks for diabetics, foods to avoid, wound care, and other such information.

In addition to generic messages, specific and personalized messages can be generated from the device memory as well, or specific and personalized messages can be generated from a central server (and accessed by the link on the portable device carried by the patient), where the central server receives information about test results and patient status. These specific personalized messages are generated in response to constantly-changing patient-related information, including blood glucose, ketone levels, meal content and timing, and patient exertion level, and in consideration of the patient's personal health profile. The personalized messages are in a form suitable for viewing by the patient, and may often include specific directives and commands, e.g., "stop exercise." Simultaneously with the specific directives and commands, the system can automatically send a new generic or educational message regarding dangers and health risks the patient may be likely to encounter based on their status. For example, if the patient's blood glucose returned to a normal level after being elevated, the generic message would change from one relating to the dangers of elevated blood glucose, to one regarding steps to maintain blood glucose near the optimal level. And if the blood glucose drops too low, the generic message would change to the dangers of low blood sugar.

As noted, the patient's personal health profile is considered in generating the specific and personalized messages for the patient. The personal health profile is generated when the patient first subscribes and enters the system, and then is iteratively and interactively updated in view of changes to, e.g., general health status, progression or improvement of glucose intolerance as well as of any other diseases or conditions, exertion limitations, and food and exercise preferences.

Both the profile and the selected messages get progressively personalized to the patient's need, as the database of patient information grows and patient reactions and preferences are monitored. See application Ser. No. 12/693,849, incorporated by reference.

The invention includes the methods of monitoring and advising, as well as a business based on the monitoring and advising, which generates revenues by having patients subscribe to the system and use it.

DETAILED DESCRIPTION

Figure 1:
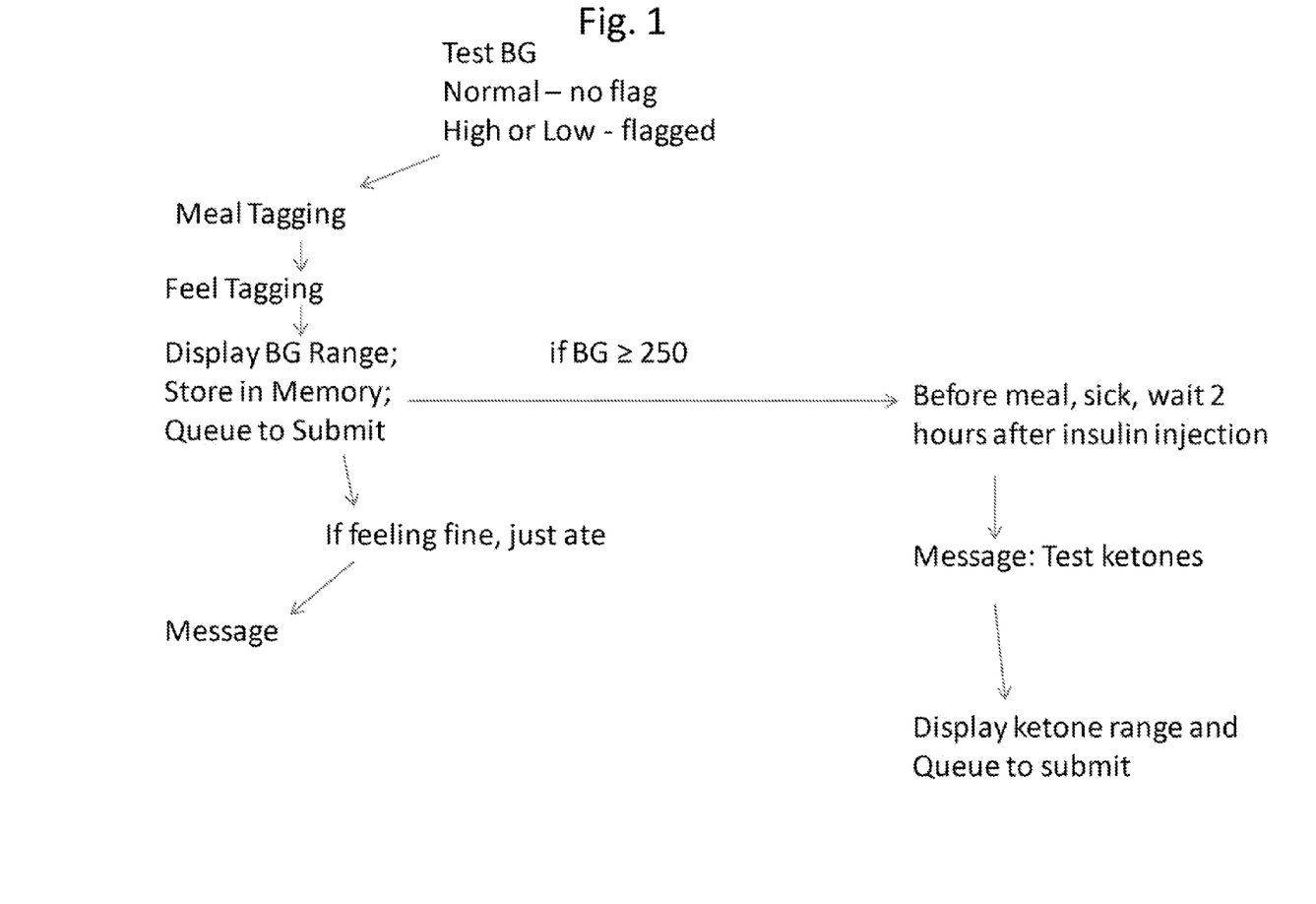
FIG. 1 is a flow diagram showing blood glucose testing and other patient input transmitted for recording and analysis, and recommendations for ketone testing and other recommendation transmitted to the patient, all transmissions being on a wireless system.

FIG. 1 shows a flow diagram of the steps in a wireless interaction where a patient inputs data including blood glucose (BG). This is preferably determined using a portable glucometer. One suitable portable glucometer is shown in U.S. Pat. No. 8,066,640, incorporated by reference. This patent also describes a combination glucometer/pedometer which can be used in the invention described herein. Other glucometer measurement devices are commercially available and also within the scope of the invention, the principal requirement being that they are portable and capable of or compatible with recording and transmission and receipt of the results of the testing and other data.

Analysis of ketone testing is also preferably carried out on the same portable device which includes the glucometer. Plasma ketones are analyzed using test strips (including but not limited to those sold as Nova Max Plus Ketone Test Strips, by Nova) and the color is preferably automatically determined on the device and analyzed.

Other analytes or metabolites related to management of diabetes include cholesterol, LDL, and others. These can also be tested conventionally and the results of the tests transmitted for recording and analysis at a central location.

The portable device also has a screen for display of advice and entry of information by the patient. Referring to FIG. 1, the patient first inserts a test strip into the appropriate port in the device (see e.g., U.S. Pat. No. 8,066,640 for a description of the strips and testing process). Preferably a next screen ("Meal tagging") is displayed which inquires: when you last ate, and optionally, other information, such as meal content, calorie breakdown among carbohydrates, protein and fats, and simple sugar content and calories.

Another screen ("Feel tagging") is also displayed inquiring as to the patient's subjective state—as patient's are often sensitive to changes in blood glucose and this input can be used effectively in forming a recommendation. Further questions about the patient's state can include whether the patient is any of: "Light headed, stressed, after exercise, ate extra food, increased medication, missed medication" and/or other input relevant to forming a recommendation.

Following analysis and display of the blood glucose level, the level is automatically stored in the device memory, e.g., in a SD memory card.

If the blood glucose is above a threshold (e.g., 250 mg/dl), the meal tagging and feel tagging information, as well as further inquiries and information, can again be requested and input by the patient. If it is more than two hours since a meal, or if the patient is feeling unwell, then the system may prompt the patient to undertake ketone testing. If the patient is feeling fine and recently ate, then a message is displayed stating, e.g., "glucose slightly high—exercise or drink water"; or, "glucose slightly low—drink some fruit juice." Blood glucose tends to be low in the morning. Similarly, a slight increase in ketone level above normal might prompt a message to drink water to address it.

The results of ketone testing and blood glucose, and patient input, are analyzed and an appropriate message is generated advising the patient; including one or more of: eat, begin exercise, stop exercise, administer medication. If a pedometer is part of the device, then the exercise (walking) by the patient can be logged and stored, along with blood glucose and ketone levels. Any or all of these parameters can be displayed on the device in a format showing changes over time, so that the effect of changes in diet, exercise, medication can be tracked.

Another feature of the system can be to track patient preferences, especially those relating to diet and exercise. The recommendations for eating can be highly specific and personalized: e.g., eat X calories of carbohydrates selected from "your favorites": mashed potatoes and pinto beans. Eat X calories of lean protein, selected from "your favorites": shrimp and egg whites. Similarly recommendations for exercise can include duration and exertion level. A heart rate monitor could also be integrated into the system to automatically input the heart rate during exercise.

An example of personalization based on a patient's original profile would be that if someone is so obese that they cannot walk, then "start walking" would not be a transmitted command in response to test results showing that the patient has elevated blood glucose. The patient's preferences for particular foods, and the patient's food dislikes, along with their preferences for exercise type, exertion level, and timing are also entered initially, and then updated as desired. All these parameters are considered in determining recommendations, educational messages, and directives to the patient.

Following transmission of each recommendation or directive, the patient's reaction to the recommended course of action, particularly the patient's blood glucose level, is recorded for monitoring. The patient's other reactions including subjective reactions, such as general well-being, lethargy, light-headedness, nausea, and headache, and other, is also recorded for monitoring. All this information may be applied in analysis and determination of further recommendations and further generic education for the patient.

Administering insulin or oral hypoglycemic agents—e.g., exenatide, liraglutide and pramlintide—can be among the specific recommendations for a patient. Administration of insulin analogues, including those which mimic real beta cell insulin (e.g., lispro, aspart and glulisine), and those which are steadily absorbed after injection instead of having a 'peak' followed by a more or less rapid decline in insulin action (e.g., Insulin detemir and Insulin glargine), can also be recommended. The recommendation could also be for one or a combination of rapid-acting, short-acting, intermediate-acting and or long-acting insulin or insulin analogues.

Also suitable for recommending to a patient is administering Metformin (including Metformin in combination with other oral diabetic medications).

Other products suitable for recommendation for administration to the patient include:

Thiazolidinediones, also known as "glitazones," e.g.: rosiglitazone (Avandia) and pioglitazone (Actos);

Sulfonylureas, e.g., tolbutamide (Orinase™); acetohexamide (Dymelor™); tolazamide (Tolinase™); chlorpropamide (Diabinese™); glipizide (Glucotrol™); glyburide or glabenclamide (Diabeta™, Micronase™, Glynase™); glimepiride (Amaryl™); gliclazide (Diamicron™); glycopyramide; gliquidone;

Meglitinides, e.g., repaglinide (Prandin™), nateglinide (Starlix™)

Alpha-glucosidase inhibitors including miglitol (Glyset™), acarbose (Precose/Glucobay™), and voglibose;

Glucagon-like peptide (GLP) agonists including Exenatide, Liraglutide, and Taspoglutide Dipeptidyl peptidase-4 inhibitors including Evildagliptin (Galvus™); sitagliptin (Januvia™); saxagliptin (Onglyza™); linagliptin (Tradjenta™); alogliptin; septagliptin pramlintade or other amylin agonists; and cinnamon; chromium supplements; vanadyl sulfate; and thiamine.

The system can also track non-diabetes related medications for the patient, and send reminders to take those medications at appropriate times. This feature is particularly useful for patients with high blood pressure, heart disease, and other chronic conditions requiring regular administration of medication. The system can also record and monitor any adverse or other reactions to such medications, and send educational messages about drug interactions, or send messages to a health-care worker to intervene and provide advice to the patient.

The recording and personalization of food preferences and dislikes is feature particularly likely to have positive impact on Type II diabetes patients. These patients are often overweight or obese and may have limited understanding of how to make positive dietary adjustment. They may not appreciate the high sugar content in most pre-packaged drinks and foods. Consuming such items can cause significant adverse reactions.

In many cases, the diabetes is eliminated or ameliorated if the patient can return to a closer to normal weight/bodyfat percentage. The necessary reduction in calories to accomplish this goal is more likely to take place if the patient is provided food choices that are more acceptable. It is also more likely if the dietary recommendations include recommended quantities of the foods for consumption, and the timing of their consumption.

In another aspect, the invention relates to uniquely tailored advice and recommendations, particular on diet, based on patient preferences. The advice and recommendations are continually updated and further refined as new information on preferences is added by the user. The individual tailoring of recommendations and advice is performed in view of the user's preferences, limitations and individualized risk assessment—as continually updated.

Figure 3:
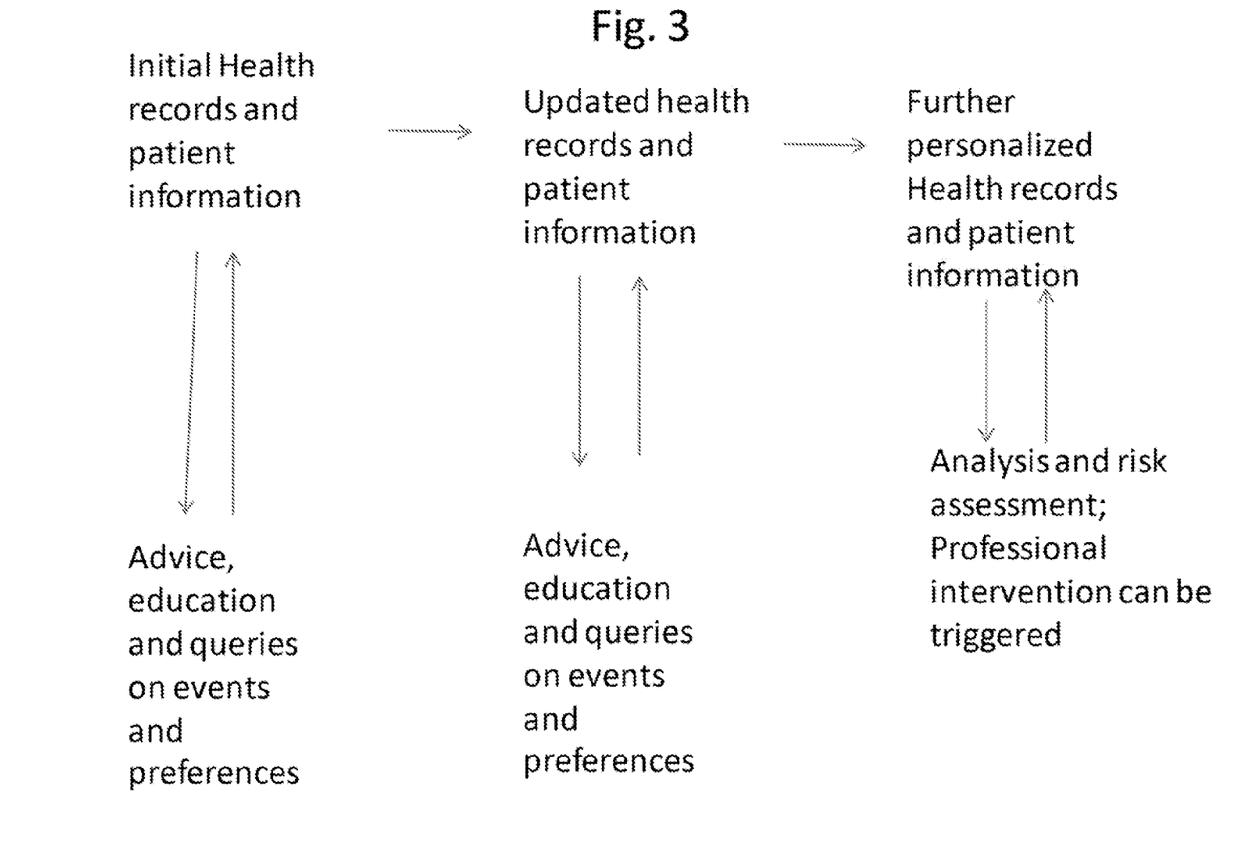
FIG. 3 depicts that a selection algorithm tailors the advice and education provided to the patient based on the patient's preferences, in a continuously updated manner.

A selection algorithm (see FIG. 3) is used to provide these preference-based advice and recommendations. The algorithm ends providing an individually tailored set of advice and recommendations which are so specific as to be a code for the individual. For example, regarding only food, exercise and education choices for an individual, the algorithm would sort and select the following criteria:

Exercise Choices:

Can individual run? (excess obesity, leg and foot condition are considerations—patient preferences)

Can individual walk? (same considerations as for running—patient preferences)

Can individual bike? (access to a bicycle, age and knowledge of how to ride—patient preferences)

Can individual swim? (access to a pool, knows how to swim—patient preferences)

Patient preferences on exercises are entered and considered and compatible exercises are recommended. For example, if a patient likes running because they prefer vigorous exercise, other vigorous exercise like swimming, mountain hiking/climbing, triathlon training, may be recommended.

Food Choices:

Avoid high calorie foods for anyone obese; avoid simple sugars for everyone.

In preferences, if a patient indicates they like corn because its soft and sweet—algorithm recommends other foods with similar attributes—e.g., yams.

In preferences, patient indicates times of the day for food preferences; e.g., eggs in the morning.

Education Choices:

Patient requests information on particular topics, e.g., best time to exercise; best foods for weight loss; foods to avoid for enhancing weight loss.

The algorithm then sorts through the information and provides uniquely tailored advice, recommendations and education for the patient. The number of selections by the algorithm quickly increases as the patient continues to provide feedback, leaving a set of instructions which is so detailed as to essentially be a unique code for the patient.

Tables 1-6 below show some exemplary patient status values, and some exemplary messages and instructions displayed on the patient's device in response.

TABLE I

| Blood Glucose Level | Response |
| --- | --- |
| <=40 | Receives a call from a call center triage to check status. Message: "Use caution. Your BG is very low. Eat a simple sugar snack (15 g carbs) and recheck BG in 15 minutes" |
| 41-70 | Message: "Your BG is below the target range. Eat a simple sugar snack (15 g carbs) and recheck BG in 15 minutes." |
| 71-110 | Message: "Great work -- BG is in the target range." |
| 111-140 | Message: "Your BG is near the target range. Make sure you check after eating." |
| 141-240 | Message: "Your BG is above the target range - Eat carefully. Monitor frequently." |
| 241-400 | Message: "Your BG is high. Check ketones. Treat as per your physician's recommendations." Unless the change from previous BG is >80 points above current reading (e.g. if prior reading was 400 and >1 hour ago, and current reading is 290, no further message is generated). |
| >400 | Receive a call from a call center triage to check status. Message: "Use caution and treat as per your physician's recommendations." |

TABLE 2

Trends in Blood Glucose

| Blood glucose Level | Response |
| --- | --- |
| 3 Readings <60 in 24-48 hours | Message: "You should seek advice from your health care provider." |
| 5 consecutive readings >240 | Message: "You should seek advice from your health care provider to address BG levels." |

TABLE 2-continued

Trends in Blood Glucose

| Blood glucose Level | Response |
|---|---|
| 3 consecutive readings >350 | Message: "You should seek advice from your health care provider to address BG levels." |

TABLE 3

Trends in Blood Glucose over 7 days

| | |
|---|---|
| 71-110 for 7 day average | Message: "7 day results: Great work - you have stayed in the target range." |
| Average BG for 7 day 111-140 | Message: "7 day results: You are staying near the target range. Make sure you check BG 1-2 hours after meals." |
| Average BG for 7 days 141-240 | Message: "7 day results: You are above the target range - Eat carefully. Monitor frequently." |
| Useful treatment tip based on trends is generated periodically | Message: "Avoid simple sugars when BG is low as well as high" |
| Supply reminder message is generated periodically | Message: "Have you ordered your test strips and lancets? Press *** or go to ____.com to order supplies." |

TABLE 4

Trends in Blood Glucose over 3 days

| | |
|---|---|
| 71-110 for 3 day average | Message: "3 day results: Great work - you have stayed in the target range." |
| Average BG for 3 day 111-140 | Message: "3 day results: You are staying near the target range. Make sure you check 1-2 hours after meals." |

TABLE 4-continued

Trends in Blood Glucose over 3 days

| | |
|---|---|
| Average BG for 3 days 141-240 | Message: "3 day results: You are above the target range - Eat carefully. Monitor frequently." |

Table 5 below shows an exemplary educational message which can be displayed in response to values received from the patient:

TABLE 5

The RULE OF 15:

If your blood glucose (sugar) is less than 70 mg/dl or if you are experiencing symptoms complete the following steps:
1) Treat with 15 gm of fast acting glucose or equivalent as listed above.
2) Wait 15 minutes and rest.
3) If your blood glucose level is still less than 70 mg/dl or if you still have symptomslisted above REPEAT steps I and 2
4) If you feel better after either the 1st or 2nd treatment then you NEED to eat the next snack or meal as indicated below:
A) If your next meal or snack is not scheduled for 30-60 minutes, eat a snack that contains 15 grams of carbohydrate. EXAMPLES:
5 crackers
a piece of fruit
slice of bread
B) If your next meal is more than 60 minutes away, eat 15 gm of carbohydrates and 1 ounce of protein. EXAMPLES:
5 crackers & loz of low fat cheese
one-half sandwich
5) If you are unable to correct hypoglycemia after two (2) treatments you need to seek IMMEDIATE medical care. DO NOT DRIVE YOURSELF.
DO NOT GIVE FLUIDS IF UNCONSCIOUS OR UNABLE TO SWALLOW:

Table 6 below displays some exemplary educational messages provided to the patient from the server.

TABLE 6

You have diabetes if your fasting glucose is 126 of greater and a random glucose is 200 or greater
When you have diabetes your sugar level goes too high because of lack of insulin, insulin resistance or both.
Normal blood sugar when you first wake up in the morning, before eating is less than 100 mg
High sugar levels can cause serious long term and short term health complications
If you have pre diabetes, lifestyle changes in meal planning, exercise and stress management can prevent or delay the onset of diabetes
With exercise your heart and blood vessels get healthier
Your body will develop endurance & strength with regular exercise. You also have a feeling of well being.
An average adult need 2 hours and 30 minutes of moderate intensity or 1 hour and 15 minutes of Vigorous intensity aerobic activity every week.
You can meet your exercise goals by incorporating several short sessions throughout the day.
You can find a physical activity to enjoy that will fit into your lifestyle.
If you have been newly diagnosed with diabetes, you may feel overwhelmed. The good news is that you can control the diabetes.
Diabetes is a self managed disease. It does require your participation for treatments.
The first step in managing your diabetes is to find a qualified specialist who works with a diabetes educator.
The second step in managing diabetes is to follow the instructions of the DM educator closely.
Learning more about diabetes will help you control your disease better.
Aerobic exercise is very beneficial to you as it can reduce the risk of coronary artery disease, hypertension, type 2 diabetes and help manage your weight and sugar levels if you do have diabetes.
Aerobic exercise helps improve your cholesterol levels and stabilizes your blood pressure.
Before you start any exercise program, talk to your doctor and get cleared to perform the activity.
Start out slowly and pace yourself. Be creative with your activity.
Know when to stop an activity. Do carry a medical ID with you all the time.
Physical activity is manual activity that develops or maintains physical fitness and overall health.
Aerobic exercise is the type of exercise that is moderate in intensity and performed for a long duration. Examples are running and bicycle riding.
Anaerobic exercise is used in non-endurance sports to build power and muscle mass. These activities are high intensity and lasts about 2 minutes.
Strength training is the use of resistance to muscular contraction to build strength, anaerobic endurance and size of skeletal muscles.

TABLE 6-continued

Flexibility exercises such as stretching improve the range of motion of muscles and joints.
If you weigh 150 lbs and you ride a bicycle at 6 mph, you will burn 240 calories.
If you weigh 150 lbs and you run at 5.5 mph, you will burn 660 calories.
If you weigh 150 lbs and you walk at 2 mph, you will burn 240 calories.
If you weigh 150 lbs and you swim at 25 yards/minute you will burn 275 calories.
If you weigh 150 lbs and you play tennis single, you will burn about 400 calories.
A snack should be planned and should NOT be eaten when you experience emotional triggers,
stress or boredom.
Plan your snacks for the time of the day when you need it the most and choose nutrient dense snack.
Examples of good snacks are fresh fruits and vegetables, 1 ounce of lean protein, ¼ unsalted nuts,
whole grain cereals and low fat or non fat dairy.
A smart snack is less than 150 calories per serving and gives you some protein.
Be sure to include calorie free beverages. You may also have sugar free jello and popsicles.
Keep track of your activity progress by using a pedometer or step counter.
Set a goal to increase your steps by 500 each day.
You must take 10,000 steps each day to meet standard recommendations.
Increase steps and activity level by parking farther away and using the stairs instead of the elevator.
Increase steps and activity level by walking whenever you can and take walk breaks at work
rather than coffee breaks.
Set a SMART goal for next month
A whole grain contains the bran, endosperm and the germ of the grain kernel.
When a part of the grain is removed during processing, it is known as refined grains. They
have lower nutritional content.
Look for 100% whole wheat, brown or wild rice, oat and whole grain corn on the label or
ingredient list.
Look for grain products that appear dense, feel heavy and contain small seeds or pieces of
whole grain that you can see.
Replace refined foods such as white bread and white rice with 100% whole wheat bread and
brown rice.
Use whole wheat pasta in casseroles, macaroni and cheese and other pasta dishes.
Snack on whole grain, low fat chips or popcorn
Cook with whole grain flour
Try to eat at least three 3 oz servings of whole grains each day.
A "free" food is any food or drink that has approximately less than 20 calories and 5 grams or
less of carbohydrate per serving.
If you eat more than 3 servings of a "free" food, be sure to count it as a carbohydrate.
Examples of free vegetables include cabbage, radish, iceberg lettuce, celery, zucchini,
green beans, carrots, etc.
Examples of free beverages include diet drinks, black coffee, broth, water, unsweetened tea
and club soda.
Watch out for the sodium content in "free" foods.
Eat a diet low in fat, sodium and cholesterol and high in fiber, fruits and vegetables.
When shopping for food, try to get most of your groceries along its perimeter. The
perimeter has the fresh fruits, vegetables, dairy, meats and some grains.
The middle aisles generally carry the convenience foods, snack foods, artificially flavored foods,
processed foods and sugar loaded items.
Healthy exceptions in the middle aisles are fruits canned in its own juice, canned vegetables,
reduced sodium soups, whole grain pasta, brown and wild rice, whole grain cereals.
Other healthy choices in the middle aisles are herbs and spices, healthy cooking oils, raw nuts
and dried or canned beans.
Plan your weekly menu and prepare your shopping list. Be sure to include healthy snacks. This will
prevent impulse buying.
Be sure to eat a snack or a light meal before you go grocery shopping.
Look at the menu and nutritional information before heading out to eat at a restaurant.
Ask for specific food items rather than ordering what is advertised.
Split meals with family and friends or place half the meal in a to-go box to bring it home.
Eat slowly. Make every bite count. Place your fork down in between bites.
Skip the chips and salsa and the high calorie dessert. Opt for fruits or side salad instead.
Feel more satisfied at meal times by using smaller plates and bowls. This fools your mind into
thinking that you are getting enough food.
Eat your meal slowly. It takes about 20 minutes for your brain to get the message that your have eaten
enough and to communicate the satiety feeling to your stomach.
Feel more satisfied at meal times by drinking plenty of non caloric beverages everyday.
Feel more satisfied at meal times by changing your eating schedule or creating one that works.
Feel more satisfied at meal times by enjoying your food. Take the time at meals to simple enjoy what
you are eating.
Keep portion sizes in check when eating out. Choose the smallest size or order a lunch sized entree
at dinner time or a child sized meal.
Make substitutions: instead of fried, choose a diabetes friendly side salad or fruit bowl. Use
fat free salad dressing rather than the regular kind.
Speak with the chef to request the food broiled, roasted or grilled rather than breaded or fried.
Watch your drinks. Order diet drinks, unsweetened tea or water. Skip the shakes, ice-cream drinks
and alcoholic beverages.
Alcohol adds empty calories to your meal and it can aggravate diabetes complications such as nerve
damage and eye disease.
Remember to enter your meals and snacks into your food journal daily
Figure out what motivates you and write it out. Post it where you can see it several times a day.
Identify one unhealthy habit and work on changing that. Once you conquer that think of the next habit
you can change.
Set realistic goals for change that are specific and have short time frame such as 1 to 2 weeks.

TABLE 6-continued

Recognize the barriers that come in the way of changing. Have a plan in place to tackle with it.
You are in the pre-contemplation stage if you are not aware that there is a problem. Educate yourself
and gather more information.
You're in the contemplation stage if you may be thinking about making a change or you know that
there is a problem.
Figure out your reasons to change and make specific plan if you recognize yourself to be in the
contemplation stage.
You're in the preparation stage if you are making a plan to change. Make specific action plans and
decide on small goals that you can achieve.
You're in the action stage if you start working on your specific plans. Get help and ideas from your
health care team.
You're in the maintenance stage if you continue working on your goals. Keep reminding yourself
of your accomplishments and how much better you feel.
Friends and family who know you well and understand your diabetes can help you through
both good and difficult times.
Health care professionals including counselors, therapists and support groups can also be part of
your support network.
You can also tap into local support groups in your area, as well as on-line resources. You doctor can
help you find resources.
Get help from family and friends by requesting a specific thing. This will remove their uncertainty
about how to help you.
Find physical activity opportunities in your community though local newspaper, internet listings,
recreation centers, fitness magazines, neighborhood HOA newsletters, local YMCA and local
AARP chapter.
You may find several individual or group activities such as walking trails, walking clubs,
soccer leagues, fitness fun runs, adult co-ed sports and fitness classes in your community.
You can try swimming, mowing the lawn, coaching a basketball or softball team, playing
Frisbee or roller skating for physical activity.
Activities like yoga, pilates, cross country skiing, stair climbing at a local track, rowing, gardening,
housework, cleaning and washing the car will contribute towards your daily activity goal.
Increase your activity level by parking farther away from entrances or taking the stairs instead of
elevator of escalator.
Check your feet every day and look for cuts, sores, blisters, bruises or redness. Use a mirror or ask a
family member to help you, if you cannot see the bottoms of your feet.
Wash your feet in warm water daily. Dry your feet gently and thoroughly, especially in
between the toes.
Do not try to cut calluses or corns or use OTC corn or wart removers. Seek help from podiatrist to
deal with such problems.
Wear shoes that fit well and allow your toes to move. Never go barefoot and avoid flip-flops,
pointed toe shoes or high heals.
Wear socks at night if your feet are cold. Do not use hot water bottles, heating pads or electric
Blankets.
Foot infections are serious. Call your doctor right away if you find a cut, sore, blister or bruise
on your foot that does not begin to heal after one day.
Keep your diabetes well managed to prevent dry skin and fend off harmful bacteria. Keep
skin clean and dry.
Use sunscreen to avoid sun burns.
Avoid very hot baths or showers and bubble baths. Use moisturizing soaps such as Dove or Basis and
use oil in water skin cream such as Lubriderm or Alpha-Keri.
Do not scratch dry or itchy skin. This can lead to infections. Moisturize your skin to prevent chapping.
Treat cuts right away by cleaning it with soap and water.
Brush your teeth twice daily to take care of your teeth. Allow about 3 minutes of brushing to clean
all your teeth well.
Use a tooth brush with soft bristles and rounded ends. Soft bristles are less likely to hurt your gums.
Floss at least once a day.
Diabetic retinopathy can lead to partial or complete blindness. Controlling your blood sugars,
blood pressure and cholesterol levels can help reduce the chances of this condition.
See your eye care professional once a year for a dilated eye exam.
To keep your eyes healthy, keep your sugars well controlled, keep your blood pressure controlled
and quit smoking, if you smoke.
You have to monitor your blood sugar levels regularly to determine if your food choices, exercise
regimen and medications are working.
The frequency of checking your blood sugar level depends on the type of diabetes you have, type
of medicines you take and how much your blood sugar fluctuates throughout the day.
You must check your blood sugar more often if you are sick, if your sugar is >200 and you have
frequent episodes of hypoglycemia.
You must also check your sugar level more if you are changing medications, meal pattern or exercise
routine.
Your fasting blood sugar should be between 70-100 mg. A fasting level is the one you take when you
have not had any food or drink for the 8 hours.
Your blood sugar should be <140, 2 hours after eating or drinking.
If you are managing your diabetes with tight glucose control, check your blood sugar level often to
prevent hypoglycemia.
Sulfonylureas are medications that make the pancreas secrete more insulin; decrease the glucose
produces by the liver and allows the cells to use insulin more efficiently.
Symptoms of hypoglycemia include feeling weak, drowsy, confused, hungry, dizzy, pale, irritable,
sweating, rapid heart beat, shakiness or experiencing a cold clammy feeling.
Watch for symptoms of hypoglycemia when taking sulfonylureas.
Glimipiride, Glipizide and Glyburide are all medications in this class.

TABLE 6-continued

Glimepiride stimulates pancreas to produce and secrete more insulin and decreases production of glucose by the liver
Glimepiride is available in 1 mg, 2 mg and 4 mg with a maximum 24 hours dosage of 8 mg.
Side effects of Glimepiride include hypoglycemia and skin rash
Glimepiride must be taken with breakfast or first main meal of the day.
Glipizide stimulates pancreas to produce and secrete more insulin and helps the body to use insulin better
Glipizide is available in 2.5 mg, 5 mg and 10 mg with a maximum 24 hours dosage of 40 mg for Glucotrol and 20 mg for Glucotrol-XL
Side effects of Glimepiride include hypoglycemia, skin rash and sensitivity of skin to sunlight
Glipizide must be taken on an empty stomach, 30 minutes prior to breakfast. It is commonly used in combination with Actos and Glucophage.
Glyburide stimulates pancreas to produce and secrete more insulin and helps the body to use insulin better.
Glyburide is available in 2.5 mg, 5 mg and 12.5 mg.
Watch for hypoglycemia, skin rash and heart burn when taking Glyburide
Glyburide must be taken with meals to reduce GI effects.
If you miss a dose of Glyburide take it as soon as you remember but skip if it is close to the next dose. You should never take two doses at once.
Pioglitazone or Actos belongs to a class of drugs called Thiazolidinediones. It works by improving body's sensitivity to insulin and decrease production of glucose and triglycerides by the liver.
Actos is available in 15 mg, 30 mg and 45 mg and it is always prescribed once daily.
Watch for hypoglycemia, anemia and edema when taking Actos
Actos must be taken with a main meal
Always plan ahead when traveling if you have diabetes.
Wear and carry diabetes identification when you travel.
Wear comfortable and well fitting shoes. Do not try to break in a new shoe when traveling
If you are flying inform the security officer that you have diabetes and you are carrying your supplies with you.
Be sure to pack non perishable foods, candy and glucose tablets in your carry on bag. Watch for any symptoms of hypoglycemia
Pack extra supplies to care for your diabetes and do not check in your medications, syringes, emereency foods and testing supplies.
When reading a nutrition facts label, start at the serving size. This will establish your portion size and determine how much nutrients you are getting.
Look at the calories and multiply the amount of calories per serving by the amount of serving you will be having.
If you consume 2 servings, then multiply 2 by total calories and if you are consuming half a serving then multiply 0.5 by total calories.
Look at the total carbohydrates and multiply by your serving amount to determine how many choices of carbohydrate you are getting.
One choice or serving of carbohydrate is approximately 15 grams.
Carbohydrate counting is a meal planning tool that helps you understand how your food choices impact your blood sugar levels.
Carbohydrates affect your blood sugar more than any other foods. Glucose is the main source of energy for our body and most of the carbohydrates is digested into glucose.
Carbohydrates include grains, breads, cereals, dried beans, starchy vegetables, fruits, milk and yogurt, juice, sweets and desserts.
A serving of carbohydrate contains approximately 15 grams. Carbohydrates from any food has similar effect on blood glucose.
Foods that contain fewer than 20 calories and 5 grams of carbohydrates are considered "free" foods if a single serving is consumed.
A healthy meal plan includes 3-4 servings of carbohydrates at each meal and 1-2 servings of carbohydrate at each snack. A standard meal plan includes three meals and a bedtime snack.
When meal planning, evenly space out the meals and eat meals about the same time every day.
Use measuring cups and spoons at home to keep your portion sizes in check.
Healthy eating includes consuming a variety of foods from each food group and each meal should be about the same amount of food.
All foods can be included in a meal plan for diabetes as long as you are particular about the portion sizes.
The DASH diet eating plan is used to lower blood pressure. This plan is based on eating fruits, vegetables, low fat or non fat fairy and much less sodium than any standard meals.
The DASH plan recommends consuming 6 to 12 servings of grains and grain products of which at least 3 choices are whole grains. It has limited amount of fats
The DASH plan recommends 4-6 servings of fruits and vegetables and 2-4 servings of low or non fat dairy.
You can have about 1.5 to 2.5 servings of lean meats, fish or poultry per day and 3-6 servings of nuts, seeds and legumes each week.
Pack medical supplies to last 2 weeks and inspect them every 2-3 months. Replace supplies as needed.
Keep one full day's supply in a safe place at work.
Pack the following items: insulin & medicines that you take regularly, syringes & needles, test strips & lancets, glucose tablets, sharps container, insulated bag with frozen ice packs and a flashlight with new batteries.
Rapid or short acting insulin should be clear without any particles. Insulin should not have clumps, crystals or frost. When in doubt, discard.
Keep insulin away from extreme heat or cold or bright light. Insulin will keep at room temperature for up to 28 days if opened. Store out of light.
Food supplies: 1 gallon of water per person per day, 4 packs of glucose tabs, non perishable cans of food such as chicken, tuna, salmon, manual can opener & utensils, 6 cans each of sugar-free soda, regular soda, fruit juices & lite fruit juices.

TABLE 6-continued

Food supplies: 1 box of dry cereal, powdered milk, 1 jar of peanut butter and a large box of crackers
Have disposable plates, cups and napkins.
Ear medical ID or bracelet stating you have diabetes. Carry ID with you all the time.
Do not forget to check your feet daily even during a disaster. Do not skip meals and continue to take
your medications as ordered
Make a list of local telephone numbers to have handy in case of a disaster such as Red cross,
nearest hospital, emergency medical center, physician and American Diabetes Association
With diabetes, the body does not make enough insulin or the body is not able to use the insulin
properly.
Retinopathy is the disease of the eye. If the blood sugar level is high, it causes damage to the blood
vessels of the eye resulting in blindness.
Neuropathy is the disease of the nerves. If left unchecked, this condition leads to amputations.
Nephropathy is the disease of the kidneys. If the blood sugar level is high, it leads to kidney failure
and dialysis.
Eat 3 small meals and 2 to 3 small snacks per day on a regular schedule.
Achieve or maintain a healthy weight. Many people with diabetes need to lose weight to improve
blood sugar control.
Exercise regularly. If you have diabetes, you will have extra benefit from exercise. It helps your
body to use insulin better.
Less insulin is needed when you exercise regularly.
When you exercise, there is an increased absorption and effectiveness of insulin.
You only need to reduce your insulin by 1 to 2 units if you do mild exercise like walking or bike riding.
Reduce insulin by 4 to 8 units for moderate to heavy exercise
Talk to your doctor to adjust insulin doses when you start to exercise
Safe exercise is beneficial in managing diabetes regardless of your age
If you are elderly and have diabetes, walking is your best option.
Be sure to start the program under the supervision of your physician, if you have not exercised
for a long time.
Elderly persons with diabetes should avoid exercising in too hot or too cold weathers to prevent
heat or cold injury.
Focus on mild to moderate activity as the body takes longer to repair itself. Exercise should not
cause you any pain.
Your health care team will be able to provide information for local government and non profit
agencies that provide help.
The hospital social workers can help you find aid for diabetes supplies, medicines and local & state
financial resources
Apply for state and federal programs like Medicare & Medicaid. Such programs may cover your
diabetes supplies
Visit www.dlife.com or www.diabetes.org for educational topics including financial assistance
Topics.
Look for manufacturer's coupon to buy supplies. Popular manufacturers will offer discount coupons
and samples.
Strength training can improve your quality of life as you age.
Strength training also reduces the risk of osteoporosis and stress fractures. Before you start any
exercise program, talk to your doctor.
You may start the program with moderate activity, about three times per week with one set of 10 to
15 repetitions.
The ADA recommends strength training for people with type 2 diabetes to improve control of
sugar levels.
Consult with a physical therapist or personal trainer to learn correct postures to do the training activity.
Find more information at American Diabetes Association www.diabetes.org
Find more information at the website of the National Institute of Diabetes and Digestive and Kidney
Diseases
Find more information at www.diabeteshealth.com & www.diabetesnet.com
Find more information at National Diabetes Education Program
http://www.ndep.nih.gov/resources/index.aspx
Find more information at American Dietetic Association www.eatright.org
Find more information at Diabetes Education and Research Center
http://www.diabeteseducationandresearchcenter.org
Develop a S.M.A.R.T goal. The acronym stands for: S: specific, M: measurable,
A: attainable, R: relevant, T: time frame
Specific: You must set specific goals rather than vague goal. It should have a full description.
Measurable: You must set goals that can be measured.
Attainable: Your goals should be reasonable and achievable.
Relevant: Your goal must be realistic and applicable to your current state.
Timely: Each goal should have a time frame to limit it. This way you will be able to track your
performance and progress.
Keep you blood sugar level within normal range to preserve your kidneys.
Screen for kidney disease yearly. You may be able to slow down the progress if the
kidney disease is spotted early on.
Daily exercise helps lower your blood sugar and blood pressure. This in turn preserves your
kidney functions.
Smoking decreases blood flow to the kidneys and interferes with insulin. Quitting will help with
either of these and preserve the kidneys
Eat a balanced, healthy meal. Choose fresh foods whenever possible. Avoid fried foods and
foods with lot of additives.
Losing weight can help you manage diabetes better.
Figure out how much weight you must lose to get to your ideal body weight or a healthy BMI
and set a realistic time frame.

TABLE 6-continued

Losing 1 to 2 pounds per week is healthy. So if you have to lose 20 pounds, then give yourself 10 to 20 weeks to get there.
Continue to eat 3 small meals and 1 to 2 snacks daily, but change in the quantity of the food.
You may choose foods like baby carrots, celery sticks and other calorie poor but nutrient rich foods as part of your meal plan.
To have a healthy weight loss, you must include some form of physical activity of about 30 minutes daily.
Create a plan with your health care team to manage diabetes and avoid slipping up too much with your diabetes care.
Cope with diabetes in a healthy way! Relax by playing or listening to music.
Avoid negative thinking about diabetes and self talk positively. Talk to family and friends.
Do something that will take the focus away from diabetes. Walking, dancing, cleaning the house or watching a movie can help.
Help someone else or volunteer. This will take the focus from your disease state. Write a blog or in a journal.
Being indifferent about diabetes care at work may put you at risk and compromise your overall health and safety.
Tell your employer that you have diabetes and show your supervisor your cafe plan.
Ask for regular breaks, a place to store and take your insulin or other medicine.
The American Diabetes Association offers counseling to help you teach your rights on the job.
The ADA has samples of letters that you can write to your employer or human resource representative to make accommodations at your work place.
Carry a backpack, briefcase, or large purse that always contains your at-work essentials, such as medications, snacks, etc.
A person with well managed often miss fewer days due to illness.
Carbohydrates have the highest impact on the sugar level.
Liquids containing carbohydrates like milk and juice will increase your sugar level faster than solid carbohydrates such as bread.
Eating a larger portion will make your blood sugar level to raise more when compared to eating the same food in a smaller portion
Sugar levels are affected by the timing of meals & snacks. Eating 3 meals & 2 snacks daily at the same time will keep it steady.
It is also important to eat the same amount of carbohydrates at each meal so it can match with your medications.
Peripheral neuropathy is a complication of high sugar levels that damages the blood vessels and nerves in your legs and feet.
Peripheral neuropathy results in numbness and pain. By staying active, you can help keep the pain minimal.
Low impact aerobic activities such as walking, swimming & water aerobics are good, if you have peripheral neuropathy.
Maintaining the suppleness of the leg muscles is very important if you have peripheral neuropathy.
Always, remember to wear comfortable footwear. Check your feet often to make sure there are not minor injuries.
If you like fast foods, you may include them with a little planning. Your goal is to limit the intake excess fat, sugar and salt.
Choose a single patty hamburger with no cheese and have a side salad instead of fries. Have a diet drink.
When ordering a salad, ask for diet dressing and add some crackers or croutons. Limit salads made with mayonnaise.
Order a thin crust pizza and a single layer of cheese. Have Canadian bacon or ham and vegetables for toppings.
Choose grilled or baked chicken. If only deep fat fried chicken is available, remove the breading and the skin before eating.
The Glycemic Index (GI) is a measure of the effects of carbohydrates on blood sugar levels.
Carbohydrates that break down quickly and release glucose rapidly into the bloodstream have a high GI.
Carbohydrates that break down more slowly, releasing glucose more gradually into the bloodstream, have a low GI.
Foods with a high GI may cause your blood sugar level to go above the healthy level.
A low GI food will release sugar more slowly and steadily. This leads to a healthy blood sugar levels after meals.
A high GI food causes a fast rise in the blood sugar levels. These foods should be used for a person with too low blood sugar levels.
A person who is insulin sensitive requires normal or low levels of insulin to process sugars in the food.
People with diabetes usually have insulin resistance, which leads to more health complications.
There are no approved alternate therapies for diabetes because of conflicting results from various studies.
Do not stop taking the medicines that your doctor has prescribed, if you decide to try an alternative therapy.
Always discuss with your doctor any herbs or supplements that you plan to take. They may interfere with your current medicines.
If you have allergies, you can still eat healthful meals while excluding foods that you do not tolerate. Focus more on fresh foods rather than processed foods.
Processed foods or commercially prepared foods might have some allergen that could trigger your allergies.
Prepare your own meals. This way you will be able to control the ingredients you use and you will know what you are eating.
Carefully read the food labels and look for all the keywords of your particular allergy.

TABLE 6-continued

An insulin pump is a tiny computer connected to your body 24 hours a day to give you
the insulin you need.
Infusion sites can get infected, so it is important to know how to place the catheter correctly
and to keep the area clean.
Replace your infusion set every 2 or 3 days or as often as your doctor advises. Insert a new
infusion set at least 1 in. (2.5 cm) away from where the last one was.
Most insulin pumps can resist water but are not waterproof, so you need to disconnect them to
go swimming or take a shower or bath.
Sleeping with your pump is not a problem. There is no need to worry about accidentally
rolling onto your pump and changing your insulin dose.
Get into the habit of keeping good records. Having records can help you see patterns and
control your sugar level.
Meditation is a type medicine that balances the body and mind. It can produce a deep state
of rest and a calm mind.
During meditation, you focus your attention on one thing and remove all other thoughts
from your minds.
Emotional benefits of meditation include gaining a new outlook on stressful situations and stress
management.
Meditation can help if you have diabetes by allowing you to manage diabetes in a more composed
and calm manner.
Meditation exercises: Breathe deeply, Scan your body, Repeat mantra or a relaxing phrase,
Walk and meditate, Engage in a prayer, Read and reflect
A diabetes diet simply means eating a variety of nutritious foods in sensible portions and sticking
to regular mealtimes.
Diabetes diet is a healthy-eating plan that is high in nutrients and low in fat and calories.
It focuses more on fruits, vegetables and whole grains.
Get most of your glucose from complex starches such as fruits, vegetables, whole grains, legumes
such as beans, peas and lentils and low-fat dairy products.
Fiber cannot be digested by your body and it is not absorbed. Having fiber in your diet lowers the risk
of heart disease.
Good sources of fiber include vegetables, fruits, nuts, legumes, whole-wheat flour, wheat bran and
other grains such as oatmeal and barley.
Fish is a good alternative to other high fat meat. Cod, tuna and halibut are good choices.
Foods containing monounsaturated and polyunsaturated fats such as avocados, almonds, pecans,
walnuts, olives and vegetable oils are good for your heart health.
A diabetes meal plan is not a restrictive meal plan. It is in fact a healthy plan that everyone can follow.
You may be using the exchange system, carbohydrate counting or glycemic index for your meal plans.
Choose foods that are high in fiber, protein, vitamins and other minerals. For example, if the recipe
Calls for all purpose flour, substitute is with whole wheat flour.
Choose fresher and whole foods whenever possible.
Always look for fresh fruits, vegetables and meat. If you cannot find a fresh option, choose a
frozen variety.
Use liquid oils in place of solid fats. If your recipe calls for butter, lard or shortening - choose trans
fat free margarine or vegetable oils.
Use low fat dairy product instead of regular dairy. If the recipe calls for whole milk or yogurt,
use fat free milk or low fat yogurt.
Salt and sugar are useful and readily available flavorings. Instead of using them in a recipe, try
using herbs and spices
to improve flavor.
Spices like cinnamon, nutmeg, cardamom, vanilla, vinegar and flavored mustards can be used
in baked or cooking to give the food an additional flavor.
An insulin pump frees you from a strict regimen of meals, sleep, and exercise because you
can program it to match your changing schedule.
With a pump, you do not have to stop what you are doing to give yourself a shot. You just push
a button to give yourself a dose.
A pump may help you keep your blood sugar closer to normal. People who use a pump have fewer
big swings in their blood sugar levels.
People who use a pump may have fewer problems with very low blood sugar. This is especially true
overnight, when people go the longest time without eating.
Some people keep their pumps connected when they go swimming, but most pumps are not
waterproof. You may be able to put yours into a waterproof case.
If you need to disconnect your pump for sports, give yourself a bolus to cover the basal rate that you
will miss while you are disconnected.
Hypoglycemia is when your blood sugar level drops to dangerous levels. You should learn to
Recognize the signs of hypoglycemia to prevent this from happening.
Signs of hypoglycemia include hunger, shakiness, sweating, confusion, dizziness, anxiety or weakness.
When you first start exercising, you must check your blood sugar before, during and after exercise.
Exercise at a later time or give yourself an additional insulin dose, if your sugar level is greater than
200 mg/dL.
Eat a snack before starting to exercise if your sugar level in normal range
Use insulin, snacks, or glucose tablets to adjust blood sugar level after exercising.
Stress can make it harder to control your blood sugar level, which will increase the risk of problems
from diabetes.
Stress can distract you so much that you may forget to take your medications or pay attention
to you care.
Autogenic training uses visual imagery and body awareness to move you into a deep state of
relaxation.
Breathing: You place one hand your chest and the other on your stomach. Take in a slow,
deep breath, taking in as much air as you can.

TABLE 6-continued

For Progressive muscle relaxation, you would slowly tense and then release each muscle group individually.
Fasting is possible for people with diabetes depending on their personal health status.
If you take medications to control your sugar level, you may be at a higher risk with fasting.
Do not go on a "dry" fast, if possible. A person with diabetes should not fast for more than 12 hours at a time. Break the fast as soon as possible.
If you were ever diagnosed with ketoacidosis, you must consider NOT fasting.
If you are diagnosed with heart disease or have blood pressure issues, along with diabetes, it is not a good idea to fast.
Monitor your blood sugar levels and if it is significantly high or low compared to other readings around the same time, break your fast.
When you do break the fast, split the meals in to two so that your sugar level does not spike high in a short period.
Exercise can help you manage your diabetes along with diet and medication. You can continue to exercise with diabetes.
Carry ID with you all the time. The ID should have your diagnosis and emergency contact information.
Watch for low blood sugar level. Keep a source of sugar such as hard candy, mints or glucose tablets with you all the time.
You must not exercise if you blood sugar level is greater than 250 mg/dl. You must wait until your blood sugar level is lower.
Start the activity slowly and increase slowly. Do not strain yourself Be aware of your heart rate.
Stop exercising if you feel any pain in the chest, faintness, queasiness or fuzzy vision.
The best time to exercise is 1 to 3 hours after meals. You should avoid exercising when your insulin is peaking.
Wear comfortable shoes when exercising.
Most holiday meals and treats are high calorie, sugar laden delights.
Be picky about treats and events
Watch out for the free calories
Beware of the Extra helping
F is for FUN not food
Bring a healthy item
Exercise as usual or more
If your blood sugar level is out of range most of the time, it can damage the blood vessels and the nerves which can hamper sexual performance and enjoyment.
Diabetes can cause nerve and artery damage in the genital area. This interrupts the blood flow necessary for an erection.
Nerve damage from diabetes can cause vaginal dryness in women. This can make the intercourse uncomfortable, even painful.
Diabetes related nerve damage can also lead to loss of sensation in the genital area which may make orgasm difficult or impossible to achieve.
Accurate diagnosis of the sexual dysfunction will help in treating the cause and improving the quality of your life.
Choose whole foods, fresh fruits and vegetables, beans and high fiber carbohydrates instead of simple carbohydrates.
Always choose low fat dairy and lean meats and proteins.
Limit overall fat intake and choose heart healthy fats.
Set times for meals and stick with it. Eat 3 small meals and 3 small snacks throughout the day to maintain your sugar level.
Use a smaller plate, such as a 9-inch plate or a salad plate instead of the regular dinner plate.
Half of your plate should consist of vegetables. A quarter of your plate should be lean proteins and the other quarter should be complex carbohydrates such as whole grains, corn or beans.
Hyperglycemia is a dangerously high blood sugar level.
It is important that you eat the same amount of carbohydrates at each meal and keep your meal times consistent.
The exchange system groups foods into categories such as carbohydrates, meats and meat substitutes and fats. One serving in a group is called an "exchange".
An exchange has the same amount of carbohydrates, protein, fat and calories as a serving of every other food in that same group.
Carbohydrates that break down quickly and release glucose rapidly into the bloodstream have a high GI.
Carbohydrates that break down more slowly, releasing glucose more gradually into the bloodstream, have a low GI.
You can plan your meals based on your health goals, tastes and lifestyle.
Flexibility exercises will help your joints stay flexible.
Flexibility exercises help keep your joints flexible. It also reduces your chance of injury during other activities.
Stretching keeps your muscles agile, toned, and streamlined. It also helps in reducing stress and promotes a greater sense of well-being.
Use a full range of motion around the joints when stretching and stretch all parts of your body two or three days per week.
Complete at least one stretch for every major muscle group. Try to hold the stretch for 15 to 30 seconds.
Stretch on both sides of the body equally.
Breathe deeply during all stretching activity. Do not hold your breathe during this activity
Aspirin decreases your blood's ability to form clots. Your doctor may advise you to take aspirin daily as part of your diabetes treatment.
Research has shown that aspirin helps reduce the risk of heart attacks and clot related strokes if you have had a previous episode of heart disease.

TABLE 6-continued

A low-dose aspirin should be used by men >50 and women >60 with diabetes and have other risk factors for heart attacks and stroke.
A daily aspirin is not recommended for men under 50 and women under 50 who have no other risk factors.
A low dose aspirin or a baby aspirin is enough to provide the protection against clot related heart disease.
Mexican - choose fajitas, whole wheat tortilla, avocado and soft tacos. Avoid taco salad, cheesy foods, chips and salsa and fried or crispy foods.
Thai - choose stir fried and sauteed dishes, brown rice and grilled meats. Avoid fried dumplings and pad thai.
Italian - choose pasta primavera and red sauce, have dressing on the side and choose lean meats.
Avoid creamy sauce, cheese filled pasta dishes and breaded or cheese blanketed meats.
Japanese - Choose fish, teriyaki dishes and sushi rolls with cucumber, tofu or avocado.
Avoid sushi rolls with deep fried fish and cream cheese, tempura dishes, and fried spring rolls.
Chinese - choose broth soups, steamed dishes with vegetables. Avoid large portions of rice and Noodles and deep fried egg rolls.
Indian - choose legumes, meats without sauces, basmati rice and whole wheat chapatti. Avoid things made with ghee, cream and fried foods.
Your risk of getting depression goes up if you have diabetes. You also have a higher risk of getting diabetes if you are depressed.
Depression is a chronic illness that usually requires medical & psychological treatment and counseling for a long time.
Signs of depression include loss of interest in normal activities, feelings of sadness or misery, and unexplained bodily problems like back pain or headaches.
Join a support group. Connecting with others facing similar challenges can help you cope.
Learn ways ays to relax and manage your stress such as meditation, yoga and tai chi. Structure your time.
Plan your day and activities.
Diabetes is for life and you cannot cure it only control it well.
Your healthcare team will provide you with the moral support and encouragement.
With a little practice you can focus on the good things in life such as family and friends when things go wrong and the negative feelings take over.
You may join diabetes communities or support groups to cope with diabetes.
Talk to you family members, friends, or even healthcare team if you notice any changing moods or habits.
Tight glucose control is keeping the blood sugar level as close to normal as possible.
The sugar level should be between 70 and 110 mg/DL before eating and below 180 mg/DL two Hours after eating for tight glucose control.
A sliding scale is an effective tool in managing your diabetes while you are sick.
Sliding scale is a way to get overall control of the blood sugar level.
For people with type 2 diabetes, a sliding scale is most useful when a tight control of a daily set carbohydrate meal plan is used.
Talk to your doctor about using the sliding scale method or any method for tight glucose control.
Nicotine in cigarette smoke makes the blood vessels hard and narrow. This results in less blood flow to the rest of the body.
Smoking causes long term coughing, poor athletic strength, sore throats, premature wrinkles on your face, stained teeth and dull skin.
Take deep, rhythmic breaths similar to smoking, except now you are inhaling clean air.
Spend your free time in places where smoking is prohibited such as library, theater or museum.
You may substitute sugarless gum for a cigarette. You can also try lemon drops, cloves, beef jerky, or plain popcorn.
Drink lots of non caloric and decaffeinated liquids like water, decaf tea. Pass up alcoholic beverages and coffee.
Treat yourself to a massage or take a nap. Enjoy relaxing activities instead of smoking.
Changes in meal patterns, activity levels, and time zones can affect your blood sugar levels.
Before you leave - see your doctor before you leave to discuss your travel plans and pack extra diabetes supplies and prescriptions.
Know what healthcare services are available near your destination in case you need medical attention.
Bring your doctor's name and phone number and a list of current medicines. Keep it with you at all times.
Carry and wear medical identification that states that you have diabetes.
Pack the medicines, syringes and blood sugar testing supplies in your carry on case or bag. Do not check
these supplies in as it can be damaged or lost
Pack two or more pairs of comfortable shoes if are taking a road trip. Changing shoes help prevent blisters.
Protect your feet all the time when you are walking by the pool, in the park, on the beach, or swimming in the ocean.
Traveling can be a smooth process, if you plan ahead of time.
For people with diabetes, fad diets can be dangerous.
The key for successfully manage diabetes is to keep the weight off and follow healthy eating for the rest of your life.
Fad diets often exclude certain food groups. A low carb diet might ask you to eat just proteins and fats for 6 to 8 weeks.
Fad diets can cause downward spikes in blood sugars. Reducing calories or carbohydrate content in even one meal can cause this effect.
Fad diets can cause an increase in cholesterol and blood pressure. This will increase the risk of heart disease.

TABLE 6-continued

You may rely on meal replacement plans as long as you take in to account the carbohydrate content of the meal replacement product.
Extreme liquid diets and low calorie diets are not recommended for people with diabetes.
To manage diabetes successfully and for long term weight loss and maintenance you must make changes to your lifestyle.
Artificial sweeteners are good alternatives to sugar and are considered free foods as they do not affect the blood sugar.
Saccharin is found in Sweet 'N Low ®, Sugar Twin ® and Sweeta ®. They do not work well in cooking. It is found in the pink packet.
Aspartame is found in Nutrasweet ®, Equal ®, Nutrataste ® and Sweet Mate ®. They do not cook well and is used as a table sweetener. It is found in the blue packet.
Acesulfame-K is found in Sweet One ®, Sunette ® and Swiss Sweet ®. These can be used in cooking and as table sweeteners. This is packaged in a blue packet.
Suraclose is found in Splenda ®. It works well as a table sweetener and in cooking or baking. It comes in a yellow packet.
Influenza is often called the flu and it is not just a bad cold. If it is not treated, it can lead to pneumonia.
A yearly flu shot can prevent hospitalization due to flu.
Pneumococcal disease is a serious illness that can lead to death. It can cause serious infections of lungs, the blood and the covering of the brain.
The pneumoccoccal vaccine is usually called PPV and it can help prevent this disease.
You can help prevent tetanus and diphtheria with combination shot called Td toxoid.
Talk to your doctor about any other vaccines you may need to protect against serious illness.
Glucose is the smallest form of sugar found in the blood. It is the main source of energy for the body.
Carbohydrates have more effect on blood glucose than protein or fat. The 4 types of carbohydrate foods that raise your blood sugar level are starches, fruits, dairy and sweets
Complex starches are those starches that have less than 50 percent of sugar in them. It has more fiber, vitamins and minerals.
Simple starches have more sugar in them. They are not a good source of fiber. This causes a quick rise in blood glucose level.
Choose complex carbohydrates over simple carbohydrates
Choose fresh or frozen fruits instead of fruit juices or fruits canned in sweet syrup
Eat the same amount of carbohydrate foods at each meal from day to day. Avoid consuming large amounts of carbohydrate foods at one time.
Non-starchy vegetables such as cauliflower, cucumber, onions, carrots, and tomatoes have the smallest effect on your blood sugar. Choose these for second helpings.
Foods labeled sugar free and unsweetened are not carbohydrate free. Read the label carefully before buying.
There are four types of fat - saturated, trans, monounsaturated and polyunsaturated fats.
The saturated fat and trans fat are also known as bad fats. Monounsaturated fat and polyunsaturated Fat are healthy fats.
Cholesterol can clog up arteries. This can prevent the steady supply of blood and nutrients to the heart, lungs, kidneys, liver and brain.
Monounsaturated and polyunsaturated fats help lower the "bad" cholesterol and improve the "good" cholesterol.
Vegetable oil, olive oil, nuts and grains are good sources of healthy fats.
Supplementing your diet with foods that contain omega-3 fatty acids provides with nutrients for a healthy life.
Protein has a less profound effect on your blood sugar when compared to carbohydrates.
The USDA Dietary Guidelines recommend that proteins should provide about 35 percent of the Total calories you consume each day.
Animal sources of protein include protein from meats, fish, poultry, eggs and dairy.
Be sure to choose lean meats, white cuts of poultry without skin and fat free dairy.
Plant sources of protein are beans, lentils, dried peas, falafel, hummus, nuts and soy-based products.
Plant sources of protein and dairy contain carbohydrate and therefore, eating them will cause your blood sugar levels to go up.
Animal-based sources of protein do not contain carbohydrates so they will not affect your blood sugar as intensely.
NOT inject insulin.
NOT give you food or fluids.
NOT put their hands in your mouth.
Inject glucagon.
Call for emergency help.
Diabetic educators can teach a member/friend to how to inject you with 1 vial of glucagon subcutaneously.
Notify your MD if you have three episodes of hypoglycemia within a one-week period or if one episode results in loss of consciousness.
PREVENTION: Follow meal plan & don't skip meals
Take medication as prescribed
Monitor Blood Glucose regularly
END Table 6

After educational materials are received by the patient, for example, one or more of the messages in Table 6, the patient can acknowledge receipt and understanding of the message on the portable device, or request information on the same or a different topic.

Figure 2:
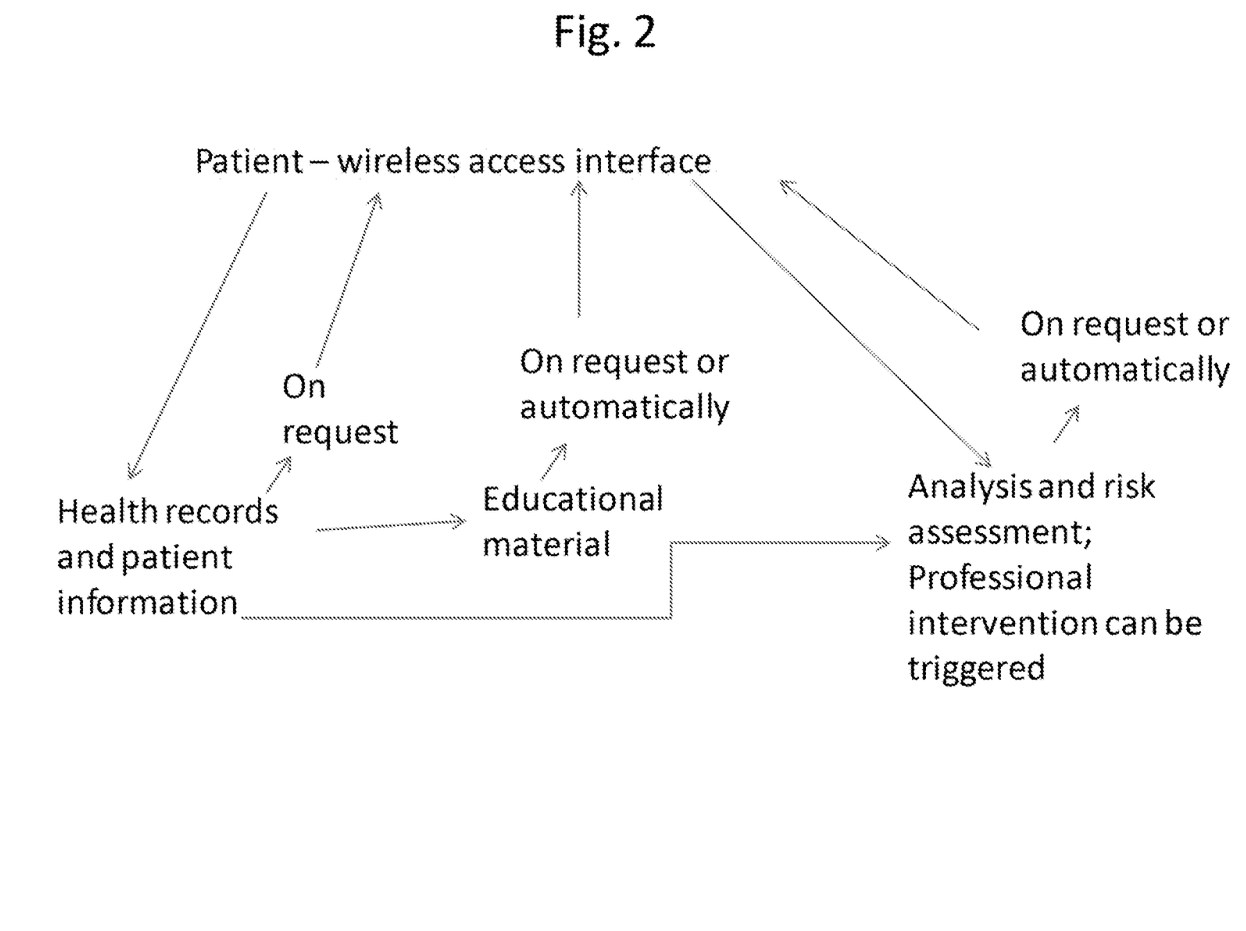
FIG. 2 depicts the wireless interface between a patient and two data repositories: health-related records and nutrition; educational; as well as between the patient and a program performing data analysis and risk assessment.

Referring to FIG. 2, the wireless interactions between the patient and his records, the educational materials which can be wirelessly accessed, and the advice and educational materials automatically provided the patient based on input and analysis, are shown. As indicated, intervention by a health care professional can be triggered by the information incoming as compared with the patient's records or with recognized treatment parameters.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, any of the terms "comprising", "including", containing", etc. are to be read expansively and without limitation. The methods and processes illustratively described herein suitably may be practiced in differing orders of steps, and that they are not necessarily restricted to the orders of steps indicated herein or in the claims. It is also noted that as used herein and in the appended claims, the singular forms "a," "an," and "the" include plural reference, and the plural include singular forms, unless the context clearly dictates otherwise. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants. The invention has been described broadly and generically herein. Each of the narrower species and subgeneric groupings falling within the generic disclosure also form part of the invention.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A method of diabetes management through a portable device carried with the patient and linked through a wireless connection to a server, wherein the patient is queried to provide blood glucose levels and other health information and the patient is periodically advised of needed actions as well as provided reminders, related advice and education, comprising:

providing the patient with a portable device with a wireless link to the server, and wherein the server is capable of sending queries for information and advice and information to the patient and is capable of receiving information from the patient and analyzing the received information to provide advice, queries and information, and wherein the portable device also incorporates a glucometer which can send the patient's blood glucose level results to the server on the wireless link, and wherein the patient enters preferences and exclusions in the server or in the portable device for types of exercise and for foods, and the patient updates said preferences and exclusions over time;

sending the patient, periodically, queries to check blood glucose level, and repeating the queries until the glucometer sends blood glucose level results to the server, which follows from the patient providing a blood sample for blood glucose level testing to the glucometer;

querying for information from the patient including time from last food intake and insulin or drug administration, and glucose-response related feelings;

advising the patient to determine ketone levels if the patient's blood glucose is above a threshold or other patient information indicates it is prudent to do so, and where the ketone level results are transmitted by the portable device to the server;

advising the patient, from the server, to either: (i) cease exertion or (ii) begin a preferred type of exercising based on: (i) patient exercise preferences and exclusions, said preferred type of exercising having similar exertion levels to patient exercise preferences, and (ii) blood glucose level, time from last food intake, insulin and drug administration, and glucose-response related feelings;

advising the patient, from the server, to eat food, and advising on food choices to eat based on:

(i) patient food preferences and exclusions, wherein said food choices are also based on the time of day the advice to eat is provided and patient preferences include patient preferences for certain foods at certain times of day, and further including in said food choices foods with similar textures to said patient food preferences, and (ii) blood glucose level, time from last food intake, insulin and drug administration, and glucose-response related feelings; and wherein the advice from the server is triggered to provide the following message if the patient's blood glucose level is less than 70 mg/dl or if the patient is experiencing known symptoms of hypoglycemia and reports those symptoms to the server:

(i) Treat with 15 gm of fast acting glucose or equivalent;
(ii) Wait 15 minutes and rest and re-test;
(iii) If your blood glucose level is still less than 70 mg/dl or if you still have hypoglycemic symptoms REPEAT steps (i) and (ii);
(iv) If you feel better, you still NEED to eat the next scheduled snack or meal, but if your next meal or snack is not scheduled for 30-60 minutes, eat a snack now that contains 15 grams of carbohydrate; or, if your next meal is more than 60 minutes away, eat 15 gm of carbohydrates and 1 ounce of protein now;
(v) If you are unable to correct hypoglycemia after the REPEAT of steps (i) and (ii) above, you need to seek IMMEDIATE medical attention; DO NOT DRIVE YOURSELF; DO NOT RECEIVE FLUIDS IF YOU ARE UNCONSCIOUS OR UNABLE TO SWALLOW; and providing education to the patient, from the server, regarding medications, diet, exercise, blood glucose and ketone levels, and risks involved with each, based on patient food and exercise preferences and exclusions, blood glucose level, time from last food intake, insulin and drug administration, and glucose-response related feelings.

2. The method of claim 1 wherein the patient provides information including feelings, reactions to medications, exercise level, time from last food intake, time from last drug administration in response to queries.

3. The method of claim 1 wherein the blood glucose level, ketone level or other patient status indicator can trigger health care worker intervention and advice from the health care worker.

4. The method of claim 1 wherein the educational materials provided to the patient include materials relevant to blood glucose and ketone levels which expand on the dangers and solutions.

5. The method of claim 1 wherein the patient indicates that the advice and educational materials were reviewed.

6. The method of claim 1 wherein the portable device is linked to or includes a pedometer or a heart rate monitor which is also carried by the patient.

7. The method of claim 1 wherein the advice on diet and exercise includes, eat carbohydrates with a low glycemic index, or increase or decrease exertion level.

8. The method of claim 1 wherein the educational materials provided to the patient specify the risks and adverse events associated with particular medications.

9. The method of claim 1 wherein the educational materials provided to the patient include information on diseases and conditions related to diabetes, including ketoacidosis, peripheral neuropathy, atherosclerosis, depression, foot wounds, and cataracts.

10. The method of claim 1 wherein the patient preferences are updated by the patient from the portable device, and after said updating, the server provides advice to the patient on foods, exercise, and education, based on the updated preferences.

11. The method of claim 1 wherein the patient also tests for LDL and cholesterol.

12. The method of claim 1 wherein the queries and advice are in the form of text messages.

13. The method of claim 1 wherein the advice to the patient on food includes similar foods or foods with the same or similar characteristics to those the patient indicates are preferences.

* * * * *